United States Patent [19]

DiDomenico, Jr.

[11] 4,456,747
[45] Jun. 26, 1984

[54] HIGH SOLIDS COATING COMPOSITIONS BASED ON CYCLOALIPHATIC DIOLS

[75] Inventor: Edward DiDomenico, Jr., Anoka, Minn.

[73] Assignee: Henkel Corporation, Minneapolis, Minn.

[21] Appl. No.: 484,247

[22] Filed: Apr. 12, 1983

[51] Int. Cl.$^3$ .................... C08G 12/32; C08L 61/28
[52] U.S. Cl. ................................. 528/254; 525/398; 528/248; 528/252; 528/259; 528/262; 528/265; 528/266

[58] Field of Search ............... 525/515, 398; 528/254, 528/259, 266, 230, 248, 252, 262, 265; 568/822, 831

[56] References Cited

U.S. PATENT DOCUMENTS 4,195,116  3/1980  Anderson et al. ............... 525/515
4,348,543  9/1982  Rogier ............................ 568/823

*Primary Examiner*—Theodore E. Pertilla
*Attorney, Agent, or Firm*—Bacon & Thomas

[57] ABSTRACT

A composition of matter useful as a high solids coating is disclosed. The composition contains at least one cycloaliphatic diol and at least one methylolamino curing agent.

6 Claims, No Drawings

HIGH SOLIDS COATING COMPOSITIONS BASED ON CYCLOALIPHATIC DIOLS

BACKGROUND OF THE INVENTION

1. Technical Field of the Invention

The present invention is directed to compositions of matter useful as coatings and containing cycloaliphatic diols and their derivatives and methylolamino curing agents.

2. Description of the Prior Art

High molecular weight acrylic and polyester resins have dominated the coatings industry, primarily as a result of the combination of properties, i.e., film hardness, flexibility, chemical resistance, water resistance, and gloss retention, required by the industry. However, with the advent of solvent emission regulations, the industry has turned to high solids coatings. Initial work on high solids coatings was directed to lowering the molecular weight of the acrylic and polyester resins. Because polyester resins could be made at much lower molecular weights than acrylic resins, most of the interest centered on making very low molecular weight polyester polyols which could be cured with melamines and other methylolamino curing agents.

Conventional high solids polyesters are made from short chained aliphatic diol and triols such as 1,4-butandiol, 1,6-hexandiol, trimethanol propane, or glycol ether polyols. These are reacted with difunctional acids or esters such as adipic acid, maleic anhydride, and phthalic anhydride. In order to get the proper combination of hardness and flexibility in low molecular weight polyesters it is important that a combination of hard and soft polyalcohols and polyacids be used. The hard components are usually the polyfunctional acids or esters such as phthalic anhydride. These are usually aromatic or unsaturated aliphatic acids which impart rigidity to the polyester resin, which translates into film hardness. The soft component is usually the polyol, e.g., 1,4-butandiol, 1,9-nonanediol, or glycol ether polyols. One exception is trimethanol propane which promotes film hardness by increasing crosslink density. If diols such as 1,6-hexandiol or 1,4-butandiol are used then unesterified or partially esterified very low molecular weight products in the polyester resin are volatilized when the polyester resin is cured with melamines. If glycol ether polyols are used such as ethylene or propylene glycol, then the ether functionality causes water sensitivity and poor gloss and color retention. Thus, while high solids polyesters have achieved some success in reducing solvent emissions in coatings, their performance properties are generally inferior to high molecular weight acrylic and polyester resins.

As used herein, the term methylolamino denotes a compound which is the product of an amino compound and an aldehyde (usually formaldehyde, giving rise to the methyl term) and the etherified and partially etherified derivatives thereof. Thus, the term encompasses polyfunctional amino compounds of the formula:

$$(R'HN)_n-R-NHR''$$

where n is 1 or greater, R' and R" are hydrogen or other groups including cycle forming carbons and R is a carbon containing backbone.

Methylolamino curing agents including those derived from melamines, guanamines, urea formaldehydes and glycoluril, are well known in the art. See, e.g. U.S. Pat. No. 4,246,376 to DiDomenico and the references cited therein, the disclosures of which are hereby incorporated by reference.

SUMMARY OF THE INVENTION

The present invention is directed to a composition of matter which is the product of at least one methylolamino compound and at least one cycloaliphatic diol of the formula:

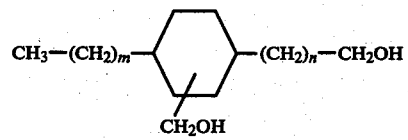

and-or certain derivatives of this diol described hereinafter, where m is an integer from 3 to 6 and n is an integer from 6 to 9 and the sum of m plus n is 12.

DETAILED DESCRIPTION OF THE PREFERRED EMBODIMENTS

The preparation of the cycloaliphatic diols used in the invention is described in detail in U.S. Pat. No. 4,348,543, to Rogier, the disclosure of which is hereby incorporated by reference. In brief, as taught by Rogier, the diols of the invention are prepared by reduction of the corresponding acids or esters which are prepared from a variety of conjugated fatty acids or their derivatives and a dieneophile through a Diels-Adler reaction.

It is further possible to react the cycloaliphatic diols of the invention with alkylene oxide such as ethylene oxide, propylene oxide and styrene oxide, caprolactone and polycarboxylic acids such as adipic acid, phthalic acid and the corresponding anhydrides, to modify water solubility and viscosity and to provide greater flexibility in the coating.

The other component utilized in forming the compositions of the present invention is the methylolamino compound. These materials are generally sold as ethers of the reaction product of formaldehyde and an amino material such as melamine, urea, thiourea, guanamines, substituted thioameline, triaminopyrimidine, 2-mercapto-4,6-diaminopyrimidine, 3,5-diaminotriazole, carbamylguanazole, 2,4-diaminothiodiazole, glycoluril, and 2-oxo-4,5-diaminoparabanic acid.

Basically, the most practial components for use herein are the melamine, urea, glycoluril and guanamine materials. Stated simply, the preparation of such material is old in the art and it is sufficient to say that formaldehyde is reacted with the amino hydrogens in varying amounts depending upon the type of resin which is desired. Thus, with melamine which contains three primary amine groups, it is necessary to react at least two of the amino hydrogens in order to form a product which will crosslink with a trifunctional alcohol. The adduct of the amino compound and the formaldehyde is ordinarily sold as an ether, in most cases that of butanol. Etherification prevents the reaction product of the amino compound and formaldehyde from crosslinking and solidifying through continued reaction of the hydroxyl group on one of the reaction products with an unreacted amine hydrogen on another molecule of the amine compound. The etherification also modifies water and organic phase solubility, lessens selfcondensation during cure, and gives a product which is less hydroscopic.

The particular advantage to using melamine based materials as the amino component is that both of the hydrogens on any amino group are available for reaction with formaldehyde, whereas when using urea it is difficult to react the second hydrogen following addition of the first mole of formaldehyde to the amino group.

Set out below are various tradenames of methylolamino compounds used in the present invention. These alcohols have been conveniently etherified with a material such as butanol or methanol or other monohydric alcohol to provide storage stability. A particularly useful material in the present invention is Cymel 303 a fully methylated melamine formaldehyde resin obtained from the American Cyanamid Company. Other useful resins also available from American Cyanamid include the melamine formaldehydes sold as Cymel 300, 301, 350, 370, 373, 380, 1116, 1156 and 1130. The benzoguamines are sold as Cymel 1123, 1125 and 1134.

The urea-formaldehyde resins included herein are available from American Cyanamid and include Beetle 60, 65, 80 and XB-1050. Partially alkylated melamine resins include Cymel 325, 370, 380, 243, 245, 248 and 255. The foregoing resins are described in a publication of American Cyanamid entitled Amino Cross-Linking Agents.

Additional methylolamino compounds include the guanamides and benzoguanamines; substituted thioameline; triaminopyrimidine; 2-mercapto-4,6-diaminopyrimidine; 3,5-diaminotriazole; carbamylguanazole; 2,4-diaminothiodiazole; 2-oxo-4,5-diaminoparabanic acid, and mixtures thereof.

The methylolamino component of the composition is generally present in amounts, by weight, up to about 90%. The diol component may be present in amounts, by weight, up to 80%. Various modifiers may be included in the composition such as pigments, flow control agents, dispersants, etc., in minor amounts.

Coatings are prepared conveniently by using the methanol or butanol adduct of the methylolamino compound which is mixed with the diol. The coating is applied by brushing, knife edge, spray or other conventional means followed by baking. Acid catalysts are employed at low levels to effect the cure.

The composition of the present invention as previously noted is highly useful in forming coatings, particularly coatings for laundry appliances, refrigerators, and generally for any metal requiring a protective coating. In particular, the composition of the present invention is highly useful in the area of high solids coatings requiring little or no volatile solvent in the product. It, for instance, has been extremely difficult to formulate coatings such as are described herein wherein high molecular weight alcohols are employed. That is, high molecular weight alcohols are ordinarily solid materials. However, using the components described herein, liquid coating compositions which exceed 70% solids and in some cases up to 100% solids can be obtained using conventional coating equipment such as high-speed electrostatic disk applicators, conventional spray equipment, and hand application such as brushing.

The composition of the invention exhibits additional advantages over other high solids by virtue of the properties of the cycloaliphatic diol component. More specifically, the cycloaliphatic diol component has no unsaturation which might detract from color or gloss retention, no ether linkages which might detract from chemical resistance or color and gloss retention, no ester linkages which might detract from chemical resistance, no secondary hydroxyl groups which might cause an incomplete or slow cure, no aromatic groups to detract from gloss and color retention on weathering. Conversely, the cycloaliphatic diols of the invention have high molecular weight and a low vapor pressure which combines to give a highly crosslinkable film, one primary hydroxyl which is attached to a cyclohexane ring which promotes film hardness, and one primary hydroxyl which is attached to a long carbon chain which promotes film flexibility. Finally, because the cycloaliphatic diols are water insoluble, they introduce no water sensitivity into the cured film. However, they can be easily emulsified or modified with propylene or ethylene oxide to render them water soluble, for use in water based coatings.

To further illustrate various aspects of the invention, the following Example is provided, it being understood that its purpose is entirely illustrative and in no way intended to limit the scope of the invention.

In the Example, the following ASTM testing procedures for coatings were used:
1. Pencil Hardness—ASTM D 3363-74
2. Adhesion Cross Hatch 20 lb. Tape—ASTM D 3359-76
3. Flexibility Forward and Reverse Impact—ASTM D 2794-74

EXAMPLE

A 21 carbon cycloaliphatic diol of the formula:

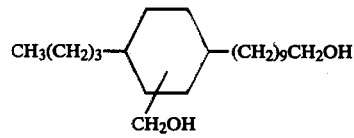

was prepared as described in Examples I–III of U.S. Pat. No. 4,348,543, to Rogier.

This diol was used to prepare melamine coatings as shown below:

| Melamine Used: | Cymel 303 | Cymel 303 | Cymel 303* |
|---|---|---|---|
| Ratio of Diol (XXI) Melamine: | 70/30 | 40/60 | 60/40 |
| Cure Temperature: | 150° C. | 150° C. | 150° C. |
| Cure Time: | 30 min. | 30 min. | 30 min. |
| Pencil Hardness to Scratch: | HB - F | H - 2H | F - H |
| Impact: | | | |
| Forward: | 60 | 20 | 40 |
| | | 40 | 60 |
| Reverse: | 40 | 1 | 5 |
| | 60 | 2 | 10 |

*Cymel 303 is a fully methylated melamine formaldehyde resin having an average equivalent weight = 160, manufactured by American Cyanamid.

From the foregoing detailed description and Example, it should be apparent that the invention encompasses a wide range of compositions. It should also be apparent that while the invention has been described in terms of various preferred embodiment, and exemplified with respect thereto, those of skill in the art will readily appreciate that various modification, changes, omissions, and substitutions may be made without departing from the spirit of the inventin. It is, therefore, intended that the present invention be limited solely by the scope of the following claims.

I claim:

1. A composition of matter which is the product of at least one methylolamino compound and at least one cycloaliphatic diol of the formula:

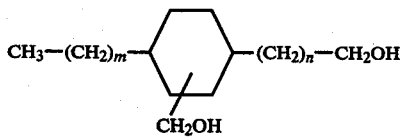

where m is an integer from 3 to 6 and n is an integer from 6 to 9 and the sum of m plus n is 12.

2. The composition of claim 1, wherein the methylolamino compound is the reaction product of formaldehyde, a member selected from the group consisting of:
(a) Melamine;
(b) urea;
(c) thiourea;
(d) guanamines and benzoguanamines;
(e) substituted thioameline;
(f) triaminopyrimidine;
(g) 2-mercapto-4,6-diaminopryimidine;
(h) 3,5-diaminotriazole;
(i) carbamylguanazole;
(j) 2,4- diaminothiodiazole;
(k) 2-oxo-4,5-diaminoparabanic acid; and
(l) glycoluril,
and mixtures thereof.

3. The composition of claim 2, wherein the methylolamino compound is etherified or partially etherified.

4. The composition of claim 1, wherein the diol compound is modified with a member selected from the group consisting of ethylene oxide, propylene oxide, styrene oxide, adipic acid, the phthalic acids and anhydrides thereof, and caprolactone and mixtures thereof.

5. The composition of claim 1, wherein said diol compound is present in an amount ranging from about 10% to about 80%, by weight, and said methylolamino compound is present in an amount ranging from about 20% to about 90%, by weight.

6. The cured product of claim 1.

* * * * *